United States Patent [19]
Martin et al.

[11] Patent Number: 5,938,120
[45] Date of Patent: Aug. 17, 1999

[54] FLUID SYSTEM AND METHOD

[75] Inventors: Rick Martin, Nevada City, Calif.; Sue Karen Pierce, Arlington, Tex.

[73] Assignee: Abbott Laboratories, Abbott Park, Ill.

[21] Appl. No.: 08/874,157

[22] Filed: Jun. 13, 1997

[51] Int. Cl.[6] .............................. B05B 15/02; B05B 1/30
[52] U.S. Cl. ......................... 239/124; 239/112; 239/113; 239/569
[58] Field of Search .................... 239/110, 112, 239/113, 124, 569, 574

[56] References Cited

U.S. PATENT DOCUMENTS

| | | | |
|---|---|---|---|
| 3,901,444 | 8/1975 | Maltbie et al. | 239/112 |
| 4,023,709 | 5/1977 | Becker et al. | 222/70 |
| 4,245,509 | 1/1981 | Mody et al. | 73/423 |
| 4,349,154 | 9/1982 | Pacht | 239/569 X |
| 4,422,576 | 12/1983 | Saito et al. | 239/693 |
| 4,424,017 | 1/1984 | Okigami et al. | 239/113 X |
| 4,457,184 | 7/1984 | Shiono | 73/864.11 |
| 4,728,034 | 3/1988 | Matsumura et al. | 239/112 |
| 5,632,822 | 5/1997 | Knipe, Jr. et al. | 134/22.12 |
| 5,723,795 | 3/1998 | Merriam | 73/863 |
| 5,856,194 | 1/1999 | Arnquist et al. | 422/64 X |

FOREIGN PATENT DOCUMENTS

| | | | |
|---|---|---|---|
| 1086211 | 9/1980 | Canada | 239/124 |
| 0409305 | 1/1991 | European Pat. Off. | B08B 9/06 |
| 0487214 | 5/1992 | European Pat. Off. | B67D 1/07 |
| 2679795 | 2/1993 | France | B05B 5/08 |

*Primary Examiner*—Andres Kashnikow
*Assistant Examiner*—Robin O. Evans
*Attorney, Agent, or Firm*—Mark C. Bach

[57] ABSTRACT

Embodiments of a fluid system and of methods of operation of a fluid system are disclosed. In one embodiment, the fluid system comprises at least one source of fluid, a nozzle and at least one first valve fluidly connecting the nozzle with the at least one source of fluid. The at least one first valve is movable between a first position where fluid flows between the at least one source of fluid and the nozzle, and a second position where fluid does not flow between the at least one source of fluid and the nozzle. A waste receptacle and at least one second valve fluidly connecting the waste receptacle with the at least one source of fluid are included. The at least one second valve is fluidly connected between the at least one source of fluid and the at least one first valve. The at least one second valve is movable between a first position where fluid flows between the at least one source of fluid and the at least one first valve, and a second position where fluid flows between the at least one source of fluid and the waste receptacle.

1 Claim, 1 Drawing Sheet

FLUID SYSTEM AND METHOD

BACKGROUND

The following relates generally to a fluid system and to a method of operation or use of a fluid system. More specifically, the following relates to a fluid system and to a method of operation or use of a fluid system in an automated instrument or other machine.

These days, some medical tests are performed by machines. Sometimes, during performance of a medical test, such machines add a liquid to a sample, such as blood and the like, contained within a tube of sorts. To add the liquid to the tube and the sample, a liquid nozzle may be used. There may be many such nozzles in a given machine.

Places at which the liquid nozzle is located on the machine may be relatively difficult to reach and to clean. Thus, in one way of cleaning the nozzle, a cleaning liquid is moved through the nozzle into an empty tube. However, this method of cleaning may require interrupting performance of medical tests. Specifically, instead of adding a liquid to a sample, time must be spent to move the cleaning liquid through the nozzle and into the tube. Also, because the tube may be used only for cleaning, moving the cleaning liquid into a tube may increase the number of tubes used by the machine. This can increase the amount of waste, i.e. tubes used for cleaning and not for medical tests, generated by the machine. Furthermore, it may be possible that an amount of cleaning fluid used may spill out of the tube. If such a spill occurs, the machine may require substantial maintenance to clean up the spill. In any case, by cleaning the nozzle in this way, time which could have been spent performing medical tests is spent cleaning the nozzle.

Similar things can happen when a fluid system, which supplies fluids to the nozzle and possibly other portions of the machine, is "primed," such as to remove bubbles from the fluid system.

Accordingly, it is desirable to provide an improved fluid system and a method of operating or using the fluid system.

SUMMARY

Embodiments of a fluid system and of methods of operation of a fluid system are disclosed. In one embodiment, the fluid system comprises at least one source of fluid, a nozzle and at least one first valve fluidly connecting the nozzle with the at least one source of fluid. The at least one first valve is movable between a first position where fluid flows between the at least one source of fluid and the nozzle, and a second position where fluid does not flow between the at least one source of fluid and the nozzle. A waste receptacle and at least one second valve fluidly connecting the waste receptacle with the at least one source of fluid are included. The at least one second valve is fluidly connected between the at least one source of fluid and the at least one first valve. The at least one second valve is movable between a first position where fluid does not flow between the at least one source of fluid and the waste receptacle, and a second position where fluid flows between the at least one source of fluid and the waste receptacle.

In another embodiment, the fluid system includes at least one source of fluid, a nozzle, and at least one first valve fluidly connecting the nozzle with the at least one source of fluid. The at least one first valve is movable between a first position where fluid flows between the at least one source of fluid and the nozzle, and a second position where fluid does not flow between the at least one source of fluid and the nozzle. A waste receptacle and at least one second valve fluidly connecting the waste receptacle with the at least one source of fluid such that the at least one first valve is fluidly connected between the at least one source of fluid and the at least one second valve are included also. The at least one second valve is movable between a first position where fluid does not flow between the at least one source of fluid and the waste receptacle, and a second position where fluid flows between the at least one source of fluid and the waste receptacle.

Other embodiments provide methods of operating a fluid system. In one such method, at least one first valve is moved toward a first position such that fluid flows between an at least one source of fluid and a nozzle both fluidly connected with the at least one first valve. The at least one first valve is moved toward a second position such that fluid does not flow between the at least one source of fluid and the nozzle. At least one second valve is moved toward a first position such that fluid does not flow between the at least one source of fluid and waste receptacle both fluidly connected with the at least one second valve. The at least one second valve is moved toward a second position such that fluid flows between the at least one source of fluid and the waste receptacle.

In a further embodiment, the fluid system comprises at least one source of fluid, a nozzle and at least one first valve fluidly connecting the nozzle with the at least one source of fluid. The at least one first valve is movable between a first position where fluid flows between the at least one source of fluid and the nozzle, and a second position where fluid does not flow between the at least one source of fluid and the nozzle. A waste receptacle and at least one second valve fluidly connecting the waste receptacle with the at least one source of fluid are included. The at least one second valve is fluidly connected between the at least one source of fluid and the at least one first valve. The at least one second valve is movable between a first position where fluid flows between the at least one source of fluid and the at least one first valve, and a second position where fluid flows between the at least one source of fluid and the waste receptacle.

DETAILED DESCRIPTION OF ILLUSTRATED EMBODIMENTS

The Figures illustrate embodiments of a fluid system 10 (FIG. 1) and 10' (FIG. 2) which may be used to supply a fluid to portions of a desired structure, such as a machine for performing medical tests and the like. The fluid supplied may be any desired fluid, such as a liquid, a gas and the like, and any construction of fluid-encountering elements of the fluid systems 10 and 10' may be chosen such that the elements do not react unintentionally with the fluid. The desired structure may be substantially similar to the structures disclosed in U.S. Pat. Nos. 5,795,784 and 5,856,194, filed on Sep. 19, 1996. Also, the fluid systems 10 and 10' may be used with other fluid handling structures and methods, such as those disclosed in U.S. Pat. No. 5,723,795 filed on Dec. 14, 1995. All of those patents are assigned to the assignee of the present case and their disclosures are incorporated herein by this reference.

While particular embodiments of the fluid systems 10 and 10' are described herein the facilitate understanding of the underlying concepts of the fluid systems 10 and 10', it is to be recognized that the fluid systems 10 and 10' may be modified in any desired manner, such as to meet requirements of a given employment and the like. Furthermore, while some methods of operation and use of the fluid systems 10 and 10' are discussed below, it is possible to use or to operate the fluid systems 10 and 10' in other ways. For instance, steps of one method of use or operation could be combined with steps of another such method to arrive at yet further methods. Also, it is to be noted that other elements can be added to the fluid systems 10 and 10' without departing from the concepts described herein.

Figure 1:
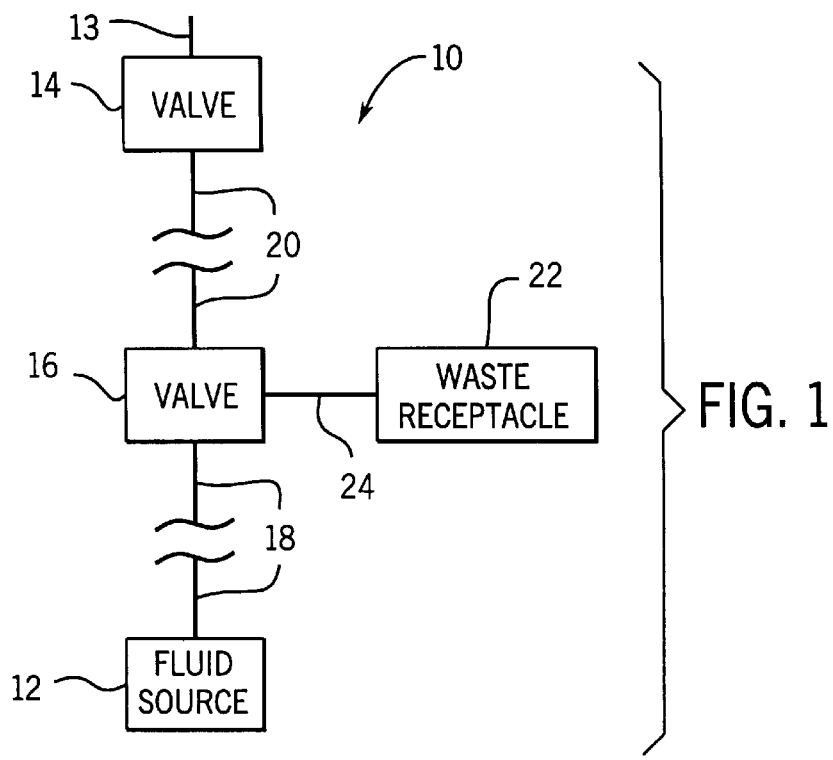
FIG. 1 is a generic schematic representation of a fluid system described herein.

Drawing attention to FIG. 1, the fluid system 10 generally comprises at least one source 12 of fluid, at least one first valve 14, at least one nozzle 13 and at least one second valve 16. In an exemplary embodiment, the at least one first valve 14 and the at least one second valve 16 may be substantially similar to valve P/N: LFVX0505750B available from Lee Co. of Essex, Conn.

The at least one source 12 of fluid is fluidly connected with the at least one second valve 16 by a first fluid conveying conduit 18. The at least one second valve 16 is fluidly connected with at least one first valve 14 by a second fluid conveying conduit 20. The at least one second valve 16 is also fluidly connected with a waste receptacle 22 by a third fluid conveying conduit 24. The at least one first valve 14 is fluidly connected with the at least one nozzle 13. The first, second and/or the third fluid conveying conduits 18, 20 and/or 24, in an exemplary embodiment, may have an inner diameter measuring about 0.031 inches. Operation of the fluid system 10 is monitored and controlled by a suitable controller, such as a computer and the like, not shown in the Figures.

The at least one source 12 of fluid may comprise a fluid supply, such as a stock bottle of fluid, a connection to a central fluid supply, i.e. directly plumbed, or the like fluidly connected with a pump for moving the fluid between the at least one source of fluid 12 and the first fluid conveying conduit 18.

The at least one first valve 14 is movable between a first position where fluid flows between the second fluid conveying conduit 20 and the nozzle 13 and a second position where fluid does not flow between the first fluid conveying conduit 18 and the nozzle 13.

The at least one second valve 16 is movable between a first position where fluid flows between the first fluid conveying conduit 18 and the second fluid conveying conduit 20, i.e. fluid does not flow between the at least one source of fluid 12 and the waste receptacle 22, and a second position where fluid flows between the first fluid conveying conduit 18 and the third conveying conduit 24 toward the waste receptacle 22. It is apparent that if the at least one first valve 14 were in its second position and the at least one second valve 16 were in its first position, then fluid may not flow between the first fluid conveying conduit 18 and the second fluid conveying conduit 20. Of course, the converse is also true.

Figure 2:
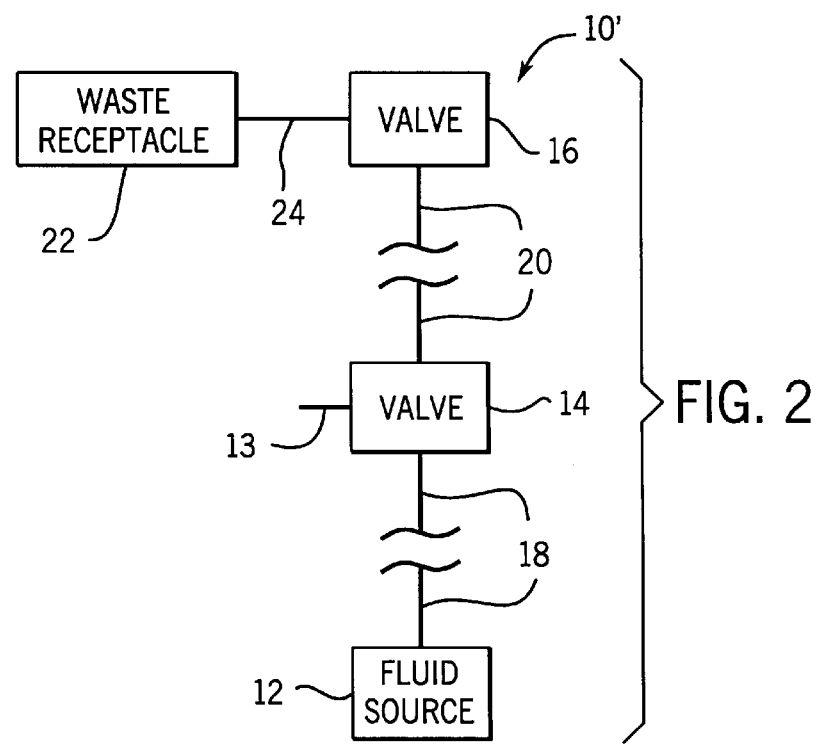
FIG. 2 is similar to FIG. 1 but shows another embodiment of the fluid system.

Referring to FIG. 2, the fluid system 10' is substantially similar to the fluid system 10, hence the like reference numerals for similar structures. However, the fluid system 10' differs from the fluid system 10 in that locations of the at least one first valve 14 and the at least one second valve 16 are exchanged. In this manner, the at least one first valve 14 is movable between a first position where fluid flows between the first fluid conveying conduit 18 and the nozzle 13 and a second position where fluid does not flow between the first fluid conveying conduit 18 and the nozzle 13. However, when the at least first valve 14 is in its second position, fluid may flow between the first fluid conveying conduit 18 and the second fluid conveying conduit 20 toward the at least one second valve 16.

In this embodiment, the at least one second valve 16 is movable between a first position where fluid does not flow between the second fluid conveying conduit 20 and the third fluid conveying conduit and from the third fluid conveying conduit 24 to the waste receptacle 22 and a second position where fluid does flow between the second fluid conveying conduit 20 and the third fluid conveying conduit 24 toward the waste receptacle 22.

With the construction of the fluid systems 10 and 10' being thusly described, operation or use of the fluid systems 10 and 10' will now be discussed in detail. Given similarities between the fluid systems 10 and 10', their methods of operation are substantially identical.

For example, during operation of the machine with which the fluid system 10 is associated, it may be desirable, at a first time period, to transfer a volume of fluid from the fluid system 10 to a container, such as a reaction vessel and the like, via the nozzle 13. This process may be called a dispense of fluid.

To do this, the at least one first valve 14 is moved toward its first position and the at least one second valve 16 is moved toward its first position. Fluid is able to move from the at least one source of fluid 12 through the nozzle 13 and into the container.

At a second time period, it may be desirable to transfer a volume of fluid from the fluid system 10 to the waste receptacle 22. This may be done to remove bubbles from the fluid system 10, to wash and/or to rinse the nozzle 13, to "prime" the fluid system 10, etc. To do this, the at least one first valve 14 is moved toward its second position and the at least one second valve 16 is moved toward its second position. Now, fluid is able to move from the at least one source of fluid 12 through the third fluid conveying conduit 24 and into the waste receptacle.

What is claimed is:

1. A method of using a fluid system in a structure for performing a process for determining an item of interest in a sample, the structure including a process path in which a reaction container is moved and with which the fluid system is operatively associated, the method comprising the steps of:

(a) providing at least one source of fluid;

(b) providing a nozzle operatively associated with the process path for directing fluid to the reaction container on the process path;

(c) providing at least one first valve fluidly connecting the nozzle with the at least one source of fluid, the at least one first valve being movable between a first position where fluid flows between the at least one source of fluid and the nozzle and a second position where fluid does not flow between the at least one source of fluid and the nozzle;

(d) providing a waste receptacle operatively associated with the at least one source of fluid;

(e) providing at least one second valve fluidly connecting the waste receptacle with the at least one source of fluid and fluidly connected between the at least one source of fluid and the at least one first valve, the at least one second valve being movable between a first position where fluid flows between the at least one source of fluid and the at least one first valve and a second position where fluid flows between the at least one source of fluid and the waste receptacle;

(f) providing a prime mover operatively connected with the process path for moving the reaction container along the process path to and from the nozzle;

(g) moving the at least one second valve to the second position such that fluid flows between the at least one source of fluid and the waste receptacle;

(h) moving the at least one second valve to the first position such that fluid flows between the at least one source of fluid and the at least one first valve;

(i) energizing the prime mover to move the reaction container along the process path to the nozzle;

(j) moving the at least one first valve to the first position such that fluid flows among the at least one source of fluid, the nozzle and the reaction container;

(k) moving the at least one first valve to the second position such that fluid does not flow among the at least one source of fluid, the nozzle and the reaction container; and (l) energizing the prime mover to move the reaction container along the process path from the nozzle.

* * * * *